United States Patent [19]

Horwath et al.

[11] B 4,001,084

[45] Jan. 4, 1977

[54] PROCESS FOR PRODUCING ISOAMYLASE

[75] Inventors: Robert Otto Horwath, Westport, Conn.; Gary William Cole, Garland, Tex.; John Anthony Lally, Stamford, Conn.

[73] Assignee: Standard Brands Incorporated, New York, N.Y.

[22] Filed: July 1, 1975

[21] Appl. No.: 592,146

[44] Published under the second Trial Voluntary Protest Program on March 2, 1976 as document No. B 592,146.

Related U.S. Application Data

[63] Continuation-in-part of Ser. No. 413,121, Nov. 5, 1973, abandoned.

[30] Foreign Application Priority Data

Oct. 31, 1974 Canada .................................. 212750

[52] U.S. Cl. .............................................. 195/65
[51] Int. Cl.² .......................................... C12D 13/10
[58] Field of Search ............................ 195/65, 66 R

[56] References Cited

UNITED STATES PATENTS

| | | | |
|---|---|---|---|
| 3,490,995 | 1/1970 | Wallenfels et al. | 195/66 R |
| 3,560,345 | 2/1971 | Yokobayashi et al. | 195/66 R |
| 3,622,460 | 11/1971 | Masuda et al. | 195/66 R |
| 3,790,446 | 2/1974 | Gunja-Smith | 195/66 R |
| 3,806,419 | 4/1974 | Heady | 195/66 R |

FOREIGN PATENTS OR APPLICATIONS 852,196   9/1970   Canada

OTHER PUBLICATIONS

Mitchell et al., J. App. Bact. vol. 32 pp. 40–50 (1969).
Manners et al., Biochem J. vol. 135 pp. 11–18 (1973).

*Primary Examiner*—Lionel M. Shapiro

[57] ABSTRACT

Flavobacterium sp. ATCC 21918 is propagated under aerobic conditions in an aqueous nutrient medium having present suitable carbon sources to produce isoamylase.

9 Claims, No Drawings

PROCESS FOR PRODUCING ISOAMYLASE

THE INVENTION

This application is a continuation-in-part of Application Ser. No. 413,121 filed Nov. 5, 1973, now abandoned.

The invention relates to a process for producing isoamylase. In particular, this invention relates to a process for producing isoamylase by propagating the microorganism Flavobacterium sp. ATCC 21918 under aerobic conditions in an aqueous nutrient medium having present suitable carbon sources.

Enzymes which affect the hydrolytic cleavage of starch are referred to in the art as amylolytic enzymes or amylases and may be derived from fungal and bacterial sources and from malt.

A number of different amylases have been identified on the basis of their particular hydrolytic effects on the amylose and amylopectin components of starch. Alpha-amylase hydrolyses the $\alpha$-1,4 linkages in both amylose and amylopectin and in commercial practice is generally used to liquefy starch to reduce its viscosity. Beta-amylase has a saccharifying effect on starch resulting from its ability to hydrolyze the $\alpha$-1,4 linkages at the non-reducing ends of the amylose and amylopectin chains and thus split off maltose units from the non-reducing chain ends. Another amylolytic enzyme, glucoamylase, hydrolyses starch to glucose. None of the aforementioned amylases, with the exception of glucoamylase, can act upon the $\alpha$-1,6 glucosidic interchain linkages in amylopectin and glycogen or their degradation products.

Amylolytic enzymes which hydrolyse the $\alpha$-1,6 glucosidic interchain linkages in amylopectin are broadly referred to in the art as $\alpha$-1,6 glucosidases. A number of enzymes having considerably different specificities have been identified in the art as being capable of hydrolysing $\alpha$-1,6 glucosidic interchain linkages. Of these, the two most important enzymes from the commercial standpoint are pullulanase and isoamylase. The major difference in regard to the specificity of these enzymes is that pullulanase will degrade the linear polysaccharide pullulan whereas isoamylase will not to any significant degree.

There are a number of patents which disclose methods of producing isoamylase and pullulanase. Canadian Pat. No. 852,196 to Ueda et al. describes a process for producing isoamylase by cultivating a strain of *Escherichia intermedia* in a fermentation medium comprising dextrin, peptone and inorganic salts. U.S. Pat. No. 3,490,995 to Wallenfels et al. discloses a process for producing cell-bound pullulanase from *Aerobacter aerogenes* in a culture medium wherein the carbon sources comprise maltose and pullulan or glycerin. U.S. Pat. No. 3,560,345 to Yokobayashi et al. describes a process for producing isoamylase by propagating *Pseudomonas amyloderamosa* in a culture medium containing as carbon sources starch, starch derivatives or maltose. U.S. Pat. No. 3,662,460 to Masuda et al. discloses a process for producing isoamylase by culturing a strain of *Aerobacter aerogenes* in a medium containing an ammonium salt and liquified starch. U.S. Pat. No. 3,790,446 and corresponding German Pat. No. 2,162,923 and Netherlands Pat. NO. 7,117,405 to Gunja-Smith disclose the production of isoamylase by Cytophaga NCIB 9497. According to Mitchell et al. (J. Appl. Bacteriol., Vol. 32, pp. 40-50, 1969) and Manners et al. (Biochem J., Vol. 135, pp. 11-18, 1973), however, the microorganism designated Cytophaga NCIB 9497 may be a Flavobacterium and not a member of the Cytophaga genus. U.S. Pat. No. 3,806,419 to Heady discloses a method of preparing pullulanase by propagating *Aerobacter aerogenes* in a medium providing as a carbohydrate source a starch or a low D.E. starch hydrolysate.

One of the most important considerations in regard to commercial production of enzymes, and specifically of isoamylase, is the yield thereof. The yields of enzymes must be such that their use is economical. In regard to microorganisms known in the art which produce isoamylase, it has generally been the case that such microorganisms produce relatively small quantities of this enzyme.

It is the principle object of the present invention to provide a process for producing isoamylase.

It is a further object of the present invention to provide a process for producing isoamylase in high yields.

These objects, and other objects of the present invention which will be apparent from the following description, may be achieved in accordance with the present invention by propagating Flavobacterium sp. ATCC 21918 under aerobic conditions in an aqueous nutrient medium having present a suitable carbon source to produce isoamylase.

Except where otherwise indicated, the bacteriological characteristics of Flavobacterium sp. ATCC 21918 were determined according to the methods described in Society of American Bacteriologists' Manual of Microbiological Methods, McGraw-Hill Book Co., New York, N.Y. (1957) and are set forth below.

Bacteriological Characteristics of
*Flavobacterium* sp. ATCC 21918

| | |
|---|---|
| Gram Reaction: | gram-negative |
| Morphology: | tapered rods, usually in pairs |
| Motility:[1] | motile, peritrichous flagella observed |
| Catalase: | positive |
| Oxidase: | negative |
| Desoxycholate agar: | no growth |
| Pigment: | no pigment produced on nutrient agar medium and on Pseudomonas P medium; soluble brown-black pigment produced in Azotomonas medium[2] |
| Fluorescent pigment: | none |
| Cellulose: | negative |
| Indole: | no growth |
| Methyl Red: | negative |
| Voges Proskauer | negative |
| Pectate: | negative |
| Mucate: | negative |
| Lipase: | negative |
| Acetate: | positive |
| Aesculin: | no growth, inhibition |
| Egg yolk: | no growth |
| Simmons citrate: | positive |
| Kosers citrate: | positive |
| Decarboxylase: | |
| Lysine: | no growth |
| Ornithine: | no growth |
| Arginine: | no growth |
| $H_2S$ Production: | negative |
| Urea: | degradation, alkaline reaction |
| KCN: | negative |
| Phenylalanine: | no growth |
| Malonate: | no growth |
| Litmus milk: | slight alkaline |
| Casein hydrolysis: | negative |
| Growth in artificial sea water medium: | no growth |
| Growth in the presence of NaCl: | |
| 5% NaCl: | no growth |

-continued
Bacteriological Characteristics of
*Flavobacterium* sp. ATCC 21918

| | |
|---|---|
| 7% NaCl: | no growth |
| 10% NaCl: | no growth |
| Temperature: | |
| 10°C: | no growth |
| 30°C: | growth |
| 37°C: | growth |
| 40°C: | no growth |
| 45°C: | no growth |
| Oxidation-Fermentation of Carbohydrates:[3] | |
| Adonitol: | growth, no pH change |
| Arabinose: | growth, no pH change |
| Dextrose: | growth, ph increased |
| Dextrose closed: | no growth |
| Cellobiose: | growth, no pH change |
| Fructose: | growth, pH increased |
| Glycerol: | growth, no pH change |
| Mannitol: | growth, pH increased |
| Sucrose: | growth, pH increased |
| Trehalose: | growth, pH increased |
| Xylose: | growth, no pH change |
| Maltose: | growth, no pH change |
| Lactose: | growth, pH increased |
| Galactose: | growth, pH increased |
| Growth Response in Peptone-free, Purple Broth carbohydrate medium:[4] | |
| Glucose: | growth, acid produced |
| Xylose: | growth, acid produced |
| Arabinose: | growth, acid produced |
| Sucrose: | growth, acid produced |
| Lactose: | weak growth, only slight acid produced |
| Mannitol: | growth, no acid produced, no fermentation |

[1] Flagella stain: E. Leifson, Atlas of Bacterial Flagellation, Academic Press (1960).
[2] Azotomonas medium: ATCC Catalog of Strains, Medium 16, p. 267 (1974).
[3] O-F Carbohydrates: R. Hugh & E. Leifson, J. Bacteriol., 66, pp. 24–26 (1953).
[4] Peptone-free Purple Broth: Ruth Gordon, Genus Bacillus Manual, USDA Handbook, No. 427 (1974).

As noted above, U.S. Pat. 3,790,446 discloses that a microorganism designated Cytophaga NCIB 9497 produces isoamylase. It has also been noted that the so designated microorganism may, in fact, be a member of the Flavobacterium genus. In order to differentiate this microorganism from Flavobacterium sp. ATCC 21918, a number of taxonomic studies were carried out on the NCIB 9497 microorganism using the methods set forth above for determining the bacteriological characteristics of Flavobacterium sp. ATCC 21918.

The bacteriological characteristics of the microorganism designated Cytophaga NCIB 9497 which are different from the bacteriological characteristics of Flavobacterium sp. ATCC 21918 are set forth below.

Bacteriological Characteristics of the Microorganism
Designated *Cytophaga* NCIB 9497 in U. S. Pat. No. 3,790,446

| | |
|---|---|
| Morphology: | ordinary rods |
| Motility:[1] | non-motile |
| Oxidase: | positive |
| Pigment: | yellow pigment produced on nutrient agar medium; no brown-black pigment produced in Azotomonas medium[2] |
| Aesculin: | growth, plus utilization |
| Urea: | no reaction |
| Casein hydrolysis: | positive |
| Oxidation-fermentation of Carbohydrates:[3] | |
| Adonitol: | no growth |
| Arabinose: | growth, pH increased |
| Cellobiose: | no growth |
| Fructose: | no growth |
| Glycerol: | growth, pH increased |
| Trehalose: | growth, sugar fermented and acid produced |
| Growth Response in Peptone-free, Purple Broth carbohydrate Medium:[4] | |
| 1 Xylose: | no growth |

-continued
Bacteriological Characteristics of the Microorganism
Designated *Cytophaga* NCIB 9497 in U. S. Pat. No. 3,790,446

| | |
|---|---|
| Arabinose: | no growth |
| Sucrose: | growth, no acid produced |
| Lactose: | growth, acid produced |
| Mannitol: | no growth |

The conditions under which Flavobacterium sp. ATCC 21918 may be propagated or grown may be varied over a relatively wide range. Depending upon the exact conditions of propagation, the isoamylase may be produced intracellularly or extracellularly. A variety of carbon sources such as maltose, glucose, etc., may be suitable for propagating the microorganism. Also, a variety of nitrogen sources, such as sodium glutamate and sodium nitrate may be used to propagate this microorganism.

The pH and the temperature of the propagation or nutrient medium may also vary but, of course, should not be such that would result in inactivating or otherwise detrimentally affecting the microorganism to such an extent that the production of isoamylase is significantly decreased. The typical pH range at which Flavobacterium sp. ATCC 21918 may be propagated is from about 5 to about 8 and the typical temperature range is from about 20° to about 36°C., but it is preferred that the microorganism be propagated in the pH range of from about 6 to about 7 and at a temperature of from about 22° to about 30°C.

In order to more clearly describe the nature of the present invention, specific examples will hereinafter be described. It should be understood, however, that this is done solely by way of example and is intended neither to delineate the scope of the invention nor limit the ambit of the appended claims. In the examples and throughout the specification, percentages are utilized to refer to percent weight/volume, unless otherwise specified.

The analytical procedure used for determining isoamylase in the following examples was performed using an automated procedure adapted from the method disclosed by Yokobayashi et al. in Biochimica et Biophysica Acta, Vol. 212, at p. 459 (1970). The procedure was modified by replacing the 1.0 percent soluble glutinous rice starch with 0.25 percent amylopectin, replacing the 0.01 M iodine-potassium iodide solution with a 0.0025 normal iodine-potassium iodide solution, and performing the procedure at a pH of 5 and a temperature of 45°C. The amylopectin substrate was prepared from waxy maize starch purified by the method described by Schoch in Methods of Enzymology, Vol. III, p. 10 (1957).

The analytical procedure is based upon the ability of debranching enzymes acting on amylopectin to form amylose. Amylose, produced by such debranching activity in a fixed time and under suitable conditions, is reacted with an iodine-potassium iodide solution to form a soluble amylose-iodine complex. The intensity of the color of the blue amylose-iodine complex is measured in a colorimeter at 610 nm and recorded on a strip-chart recorder as a peak, the magnitude of which is proportional to the debranching activity of the enzyme. Debranching enzyme activity is expressed in terms of International Units per ml of sample (IU/ml) by comparing the magnitude of the peaks obtained with those obtained with a series of pullulanase enzyme standards ranging from 0.3 to 3.0 IU/ml by the afore-described automated procedure.

EXAMPLE I

This example illustrates the process for producing isoamylase by propagating Flavobacterium sp. ATCC 21918 in an aqueous nutrient medium containing suitable carbon and nitrogen sources.

Flavobacterium sp. ATCC 21918 was propagated in a culture medium having the following composition:

Table I

| Composition of Culture Medium* | |
|---|---|
| Ingredient | Percent W/V |
| Maltose | 2.0 |
| Monosodium glutamate | 0.3 |
| $(NH_4)_2HPO_4$ | 0.3 |
| $MgSO_4.7H_2O$ | 0.05 |
| $FeCl_2.6H_2O$ | 0.001 |
| $MnCl_2.4H_2O$ | 0.001 |

*The carbohydrate constituent of the medium was sterilized separately from the other constituents.

25 ml of the culture medium at a pH of 6.8 to which the microorganism had been added was placed in a 250 ml shake flask and agitated at approximately 200 rpm. for about 70 hours while being maintained at a temperature of 30°C. and then filtered to remove the microorganisms. The cell-free broth was analyzed for isoamylase activity as described above. The broth was found to contain 21.3 IU/ml of isoamylase activity.

EXAMPLE II

This example illustrates the effect of propagating Flavobacterium sp. ATCC 21918 in an aqueous nutrient medium containing a small amount of a polyhydric alcohol.

Flavobacterium sp. ATCC 21918 was propagated under the conditions set forth in Example I in a culture medium having the following composition:

Table II

| Composition of Culture Medium* | |
|---|---|
| Ingredient | Percent W/V |
| Maltitol | 0.7 |
| Maltose | 0.2 |
| Monosodium Glutamate | 0.3 |
| $(NH_4)_2HPO_4$ | 0.3 |
| $KH_2PO_4$ | 0.1 |
| $MgSO_4.7H_2O$ | 0.05 |
| $FeCl_2.6H_2O$ | 0.001 |

Table II-continued

| Composition of Culture Medium* | |
|---|---|
| Ingredient | Percent W/V |
| $MnCl_2.4H_2O$ | 0.001 |

*The carbohydrate constituents of the medium were sterilized separately from the other constituents.

The culture medium was filtered to remove the microorganisms and the cell-free broth analyzed for isoamylase activity as described above. The broth was found to contain 49.8 IU/ml of isoamylase activity.

The terms and expressions which have been employed are used as terms of description and not of limitation, and it is not intended by the use of such terms and expressions to exclude any equivalents of the features shown and described or portion thereof, since it is recognized that various modifications are possible within the scope of the invention claimed.

What is claimed is:
1. A process for producing isoamylase, comprising propagating Flavobacterium sp. ATCC 21918 under aerobic conditions in an aqueous nutrient medium having present a suitable carbon source.
2. A process for producing isoamylase as defined in claim 1, wherein the aqueous nutrient medium contains maltose.
3. A process for producing isoamylase as defined in claim 2, wherein the pH of the aqueous medium is maintained in the range of from about 5 to about 8 during the propagation.
4. A process for producing isoamylase as defined in claim 3, wherein the temperature of the aqueous medium is maintained in the range of from about 20° to about 36°C. during the propagation.
5. A process for producing isoamylase as defined in claim 1, wherein the aqueous nutrient medium also has present a suitable nitrogen source.
6. A process for producing isoamylase as defined in claim 5, wherein the aqueous medium contains sodium glutamate.
7. A process for producing isoamylase as defined in claim 5, wherein the aqueous medium contains sodium nitrate.
8. A process for producing isoamylase as defined in claim 1, wherein the pH of the aqueous medium is maintained in the range of from about 6 to 7 during propagation.
9. A process for producing isoamylase as defined in claim 8, wherein the temperature of the aqueous medium is maintained in the range of from about 22° to about 30° C. during propagation.

* * * * *